(12) United States Patent
Berkmann et al.

(10) Patent No.: US 9,191,131 B2
(45) Date of Patent: Nov. 17, 2015

(54) METHOD FOR CONTROL CHANNEL DETECTION IN WIRELESS COMMUNICATIONS SYSTEMS

(75) Inventors: Jens Berkmann, Munich (DE); Armin Haeutle, Dachau (DE); Axel Huebner, Munich (DE)

(73) Assignee: Intel Deutschland GmbH, Neubiberg (DE)

(*) Notice: Subject to any disclaimer, the term of this patent is extended or adjusted under 35 U.S.C. 154(b) by 604 days.

(21) Appl. No.: 13/542,752

(22) Filed: Jul. 6, 2012

(65) Prior Publication Data

US 2014/0012399 A1    Jan. 9, 2014

(51) Int. Cl.
| | |
|---|---|
| *H03M 13/41* | (2006.01) |
| *H04L 27/06* | (2006.01) |
| *H04L 25/03* | (2006.01) |
| *H04B 17/309* | (2015.01) |
| *H04L 1/00* | (2006.01) |
| *H03M 13/00* | (2006.01) |
| *H04W 48/16* | (2009.01) |
| *H04B 17/21* | (2015.01) |

(52) U.S. Cl.
CPC ............ *H04B 17/309* (2015.01); *H03M 13/41* (2013.01); *H03M 13/63* (2013.01); *H04L 1/0061* (2013.01); *H04L 1/0067* (2013.01); *H04B 17/21* (2015.01); *H04W 48/16* (2013.01)

(58) Field of Classification Search
CPC ............ H03M 13/41; H03M 13/653; H03M 13/6577; H03M 13/6583; H03M 13/4107; H03M 13/3961; H04B 17/0057; H04B 1/7115; H04L 1/0054; H04L 25/03203; H04L 1/006; H04L 1/0047

USPC ............... 370/252; 375/341, 262, 265, 346; 714/795, 794, 792, 796
See application file for complete search history.

(56) References Cited

U.S. PATENT DOCUMENTS

| | | | | |
|---|---|---|---|---|
| 4,240,156 | A * | 12/1980 | Doland | 714/791 |
| 6,282,251 | B1 * | 8/2001 | Worstell | 375/341 |
| 7,340,670 | B2 * | 3/2008 | Natori | 714/795 |
| 2001/0034870 | A1 * | 10/2001 | Kravtchenko et al. | 714/769 |
| 2001/0040916 | A1 * | 11/2001 | Sato | 375/150 |
| 2003/0007270 | A1 * | 1/2003 | Bliss et al. | 360/46 |
| 2004/0001428 | A1 | 1/2004 | Datta et al. | |
| 2007/0162812 | A1 * | 7/2007 | Herrmann | 714/749 |
| 2007/0162836 | A1 | 7/2007 | Orio | |
| 2008/0092028 | A1 | 4/2008 | Orio | |

(Continued)

FOREIGN PATENT DOCUMENTS

| | | |
|---|---|---|
| WO | 2004066537 A2 | 8/2004 |
| WO | 2005079221 A2 | 9/2005 |

OTHER PUBLICATIONS

"Performance of the HS-SCCH", TSG RAN WG1 meeting #24, Paris, France, Apr. 18-12, 2002, p. 1-6.

(Continued)

*Primary Examiner* — Wutchung Chu
(74) *Attorney, Agent, or Firm* — Eschweiler & Associates, LLC (57) ABSTRACT

A method of detecting a control channel includes receiving data transmitted via a control channel. A path metric and a correction term is computed based on the received data. A decision metric representing a sum or a difference of the path metric and the correction term is computed. Based on the decision metric, it is decided on a detection of the control channel.

21 Claims, 10 Drawing Sheets

(56) References Cited

U.S. PATENT DOCUMENTS

| | | | |
|---|---|---|---|
| 2009/0028253 A1* | 1/2009 | Wu et al. | 375/260 |
| 2009/0122891 A1 | 5/2009 | Bottero et al. | |
| 2009/0207948 A1* | 8/2009 | Shimizu | 375/341 |
| 2009/0285325 A1* | 11/2009 | Zhou | 375/267 |
| 2009/0327836 A1 | 12/2009 | Shimizu | |
| 2011/0173518 A1* | 7/2011 | Jang et al. | 714/794 |
| 2013/0177064 A1* | 7/2013 | Ido et al. | 375/232 |
| 2014/0126657 A1* | 5/2014 | Nakasendo et al. | 375/259 |

OTHER PUBLICATIONS

"Further Results on SCCH Detection with Parity Bits", 3GPP TSG-RAN WG1 #27, Oulu, Finland, Jul. 2-5, 2002, p. 1-6.

"Performance of the HS-SCCH", TSG RAN WG1 meeting #25, Paris, France, Apr. 18-12, 2002, p. 1-12.

Boutillon, Emmanuel et al. "VLSI Architectures for the MAP Algorithm." IEEE Transactions on Communications, vol. 51, No. 2, Feb. 2003, pp. 175-185.

* cited by examiner

METHOD FOR CONTROL CHANNEL DETECTION IN WIRELESS COMMUNICATIONS SYSTEMS

FIELD

The invention relates to a method of detecting a control channel in wireless communications systems, for example in systems providing multiple control channels to users.

BACKGROUND

Wireless communications systems such as, for example, mobile communications systems, provide data channels for data transport in an uplink and/or downlink direction over a wireless/air interface. Further, at least one control channel is provided for controlling the data transport.

As an example of a modern communications system, a 3G HSDPA (High Speed Downlink Packet Access) may provide on a transport layer a HS-DSCH (High Speed Downlink Shared Channel), which is implemented in the physical layer by one or more HS-PDSCHs (High Speed Physical Downlink Shared Channels) representing the data transport channels. One or more HS-SCCHs (High Speed Shared Control Channels) represent the control channels for downlink packet data control from the base station (nodeB) to the user terminal. A HS-DPCCH (Uplink High Speed Dedicated Physical Control Channel) allows the user terminal (User Equipment, UE) the sending of feedback and status indications towards the nodeB.

In HSDPA, multiple users share multiple downlink PDSCH data channels and SCCH control channels. Therefore the UE has to scan a plurality of SCCHs for control information related to the UE. A reliable detection of the proper SCCH is essential for a desired system performance, e.g., high throughput.

SUMMARY

According to one aspect of the invention, a method of detecting a control channel comprises receiving data transmitted via a control channel. A path metric and a correction term are computed based on the received data. A decision metric is computed representing a sum or a difference of the path metric and the correction term. Based on the decision metric, a decision is made regarding a detection of the control channel.

According to various embodiments of the present invention, a reliable detection of a control channel can be performed. With exemplary regard to multi-channel systems, a reliable selection of a proper control channel from a plurality of control channels can be performed. Embodiments of the present invention can, for example, provide for an optimum control channel detection/selection in terms of minimizing a probability of a missed detection and/or minimizing a probability of a false alarm.

Embodiments of the present invention can provide for cost-efficient solutions in terms of fast and/or reliable control channel detection/selection as compared to conventional solutions in the field. Various embodiments of the present invention can provide for cost-efficient user terminals, wherein, for example, costs for hardware, firmware, and/or software components are minimized.

BRIEF DESCRIPTION OF THE DRAWINGS

The accompanying drawings are included to provide a thorough understanding of various aspects and embodiments of the present disclosure and are incorporated in and constitute a part of this specification. The drawings illustrate exemplary, non-limiting embodiments and together with the description serve to explain miscellaneous aspects thereof. Other aspects, embodiments, and advantages can be readily appreciated by reference to the following detailed description.

In the figures and the description, like reference numerals are generally utilized to refer to like elements throughout. It is to be noted that the various elements and structures shown in the figures are not necessarily drawn to scale. Features, elements, components, etc. are illustrated with particular dimensions relative to each other primarily for sake of clarity and ease of understanding; as a consequence, relative dimensions in factual implementations may differ substantially from those illustrated herein.

DETAILED DESCRIPTION

In the following description, for purposes of explanation and not limitation, by reference to the accompanying drawings, various embodiments are set forth including many specific details in order to provide a thorough understanding of the current disclosure. It will be apparent to one skilled in the art that other embodiments can be practiced, which differ in one or more of these specific details, without departing from the scope of the present disclosure. Accordingly, the following description is intended for illustrative, non-limiting purposes only, and the scope of the present invention shall be defined solely by the appended claims.

It will further be appreciated that the features of the various exemplary embodiments described herein can be combined with each other, unless specifically noted otherwise.

Figure 1:
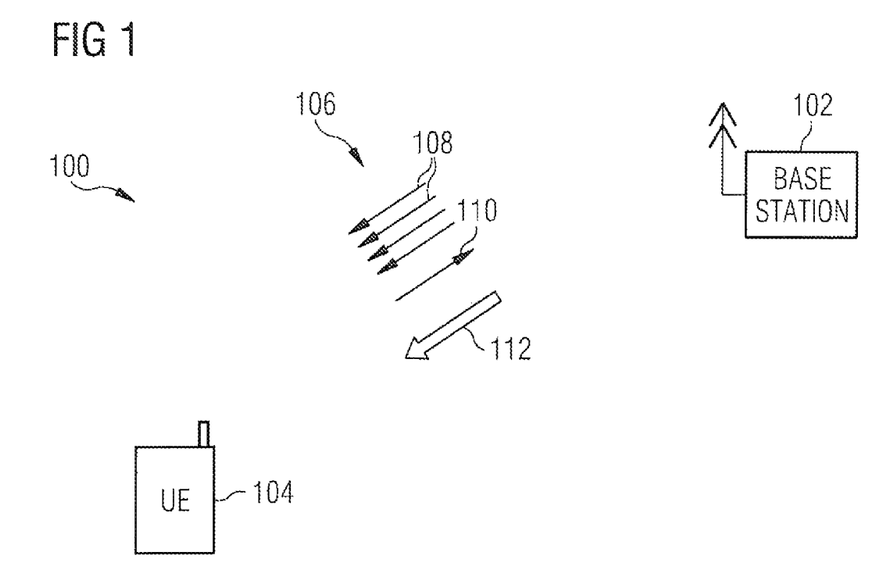
FIG. 1 is a schematic illustration of an example of a mobile communications system employing HSDPA according to the disclosure.

FIG. 1 schematically illustrates an embodiment 100 of a mobile communications system comprising a base station 102 and a user terminal (UE) 104. Data may be transmitted downlink and/or uplink via an air interface 106 between the base station 102 and the user device 104. The data may comprise control data as well as user data.

The system 100 may be implemented, for example, as a short-range wireless system such as a WLAN (Wireless Local Area Network) system, a Bluetooth system, etc., or may be implemented according to existing or future mobile communication system standards, such as GSM, CDMA, UMTS, TD-SCDMA, and/or LTE standards. Consequently, the base station 102 may be implemented as a base station for any such communication system and may therefore be implemented as a base station or wireless access point for a WLAN or Bluetooth system, a base station (BSS/BTS) for a GSM system, a GPRS system, an EDGE system, an (enhanced) nodeB for an UMTS or LTE system, etc. Likewise, the user device 104 may be implemented as a user terminal, mobile device, wireless device, mobile station, mobile phone, smartphone, etc. In any case, the base station 102 and the user device 104 may be adapted for communication with each other via the wireless/air interface 106.

Merely by way of example, the system 100 of FIG. 1 will be referred to as a 3G HSDPA system below, wherein the base station 102 may be implemented as a nodeB and the user terminal 104 may be implemented as a User Equipment UE as specified according to known HSDPA related standards. The nodeB 102 may support on the air interface 106 a HS-DSCH comprising on a physical layer one or more HS-SCCHs 108, a HS-DPCCH 110, and one or more HS-PDSCHs 112. The person of skill appreciates that the SCCH 108 may, for example, comprise from one up to four control channels. Likewise, the PDSCH 112 may comprise from one up to fifteen packet data channels.

The nodeB 102 may inform the UE 104 via one of the SCCHs 108 of future data transmissions via the PDSCH 112. Specifically, the nodeB 102 may inform the UE 104 via the SCCH 108 whether PDSCH 112 user data is scheduled for transmission, which may include data format indications such as indications on a modulation, number of OVSF (Orthogonal Variable Spreading Factor) codes, transport block size, etc. The UE 104 may send acknowledgement information as well as a channel quality indicator via the DPCCH 110 towards the nodeB 102. The quality indicator may be used by the nodeB 102 to calculate how much data is to be sent to the UE 104 in the next scheduled transmission. The PDSCH 112 may carry actual downlink user data.

The UE 104 may be informed by the nodeB 102 at HSDPA set up to monitor a number of shared SCCH control channels 108 (at most four per cell) for which the corresponding channelization codes (OVSF) may be transmitted. Further, the UE 104 may receive an UE identification (the H-RNTI, High Speed Radio Network Temporary Identifier), which the UE 104 may use to identify the proper SCCH 108 in the set of SCCHs to be monitored.

It will be appreciated that the detection of the proper SCCH 108 by the receiving part of UE 104 is prone to errors. If, due to an improper detection, an SCCH transmission is missed in the receiver, the corresponding data-carrying subframe of transport channel 112 is lost and, as a result, the data throughput is reduced. The rate of lost data can be measured by the probability of missed detection $P_{md}$. Improper channel detection may also result in the receiving part of UE 104 erroneously assuming that a data transmission in transport channel 112 be scheduled, while in fact the base station 102 has not scheduled any data transmission. As a result, power consumption may be increased in the UE 104 without data actually being received. The rate of this kind of improper detection can be measured by the probability of false alarm $P_{fa}$.

Figure 2:
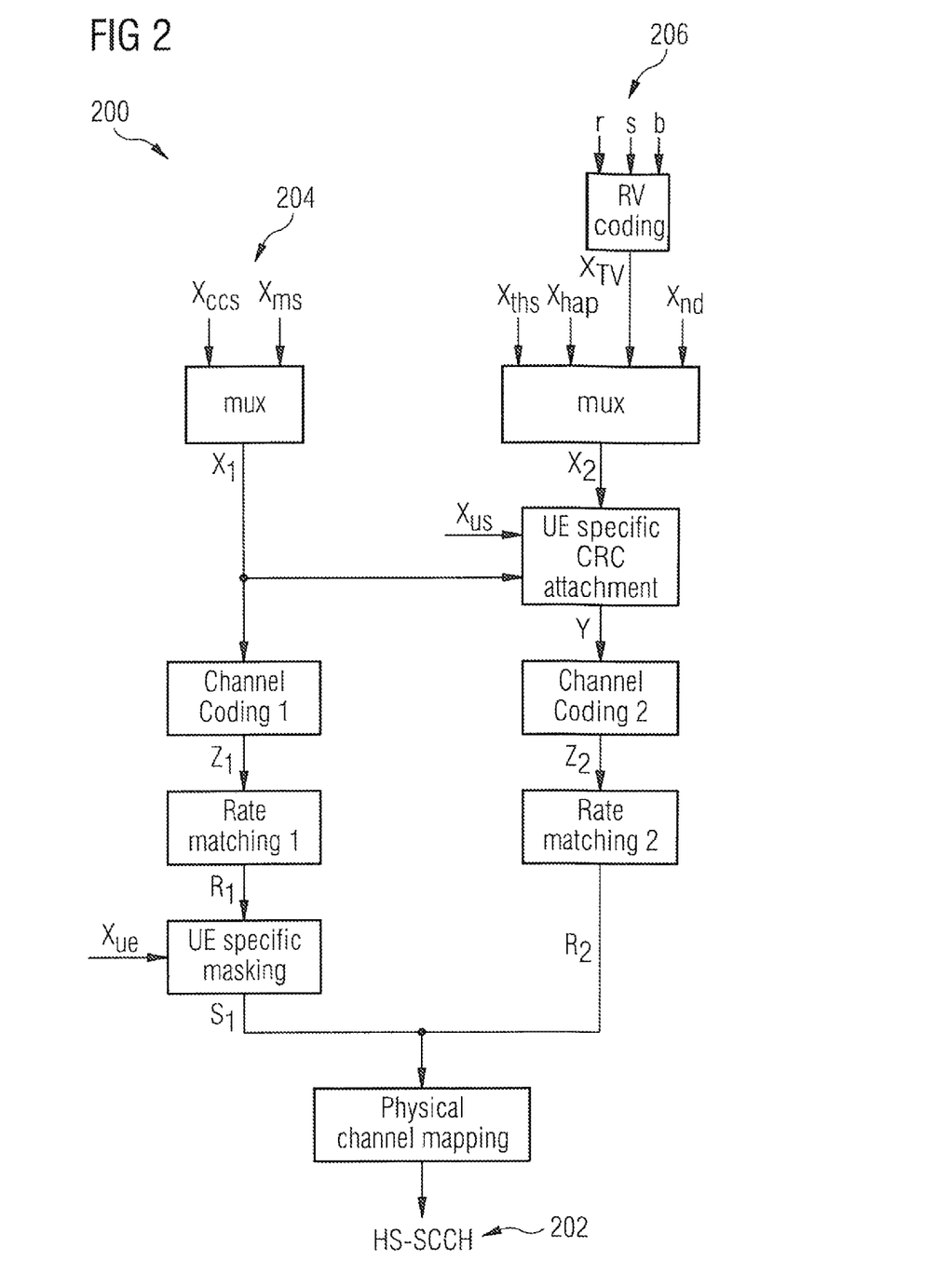
FIG. 2 schematically depicts an example of a type-1 HS-SCCH encoding according to the disclosure.

FIG. 2 depicts a coding chain 200 of a type-1 HS-SCCH 202. The information transmitted via the SCCH 202 may be split into a first part 204 and a second part 206. Part 1 204 may be transmitted in a slot 0 (i.e., a first slot) of a HSDPA subframe, while part 2 206 may be transmitted in slots 1 and 2 (i.e., a second and a third slot of the subframe). The first part 204 may comprise information Xcss and Xms required by a demodulator for the PDSCH user data in the UE. The second part 206 may carry indications of a transport block size Xtbs, a HARQ (Hybrid Automatic Repeat Request) process number Xhap, a redundancy version information Xrv, and a new data indication Xnd, etc. The second part 206 data may be required by a HARQ combiner and/or a channel decoder in a receiving part of the UE 104.

The UE-ID (H-RNTI) Xue may be input to both parts 204 and 206, wherein the UE-ID may act as a data-scrambler for the first part 204 and as CRC (Cyclic Redundancy Check) masking for the second part 206. The incorporation of the UE-ID may enable the addressing of an intended UE by the nodeB 102, as the one or more control channels SCCH 108 may be generally shared between multiple users in one and the same cell.

The type-1 HS-SCCH illustrated in FIG. 2 may be transmitted in case the UE 104 may be not configured in MIMO (Multiple Input Multiple Output) mode for the PDSCH 112. In case of an active MIMO mode the type-3 coding chain of the SCCH may slightly differ from the chain 200 of FIG. 2, as more information bits have to be carried.

Figure 3:
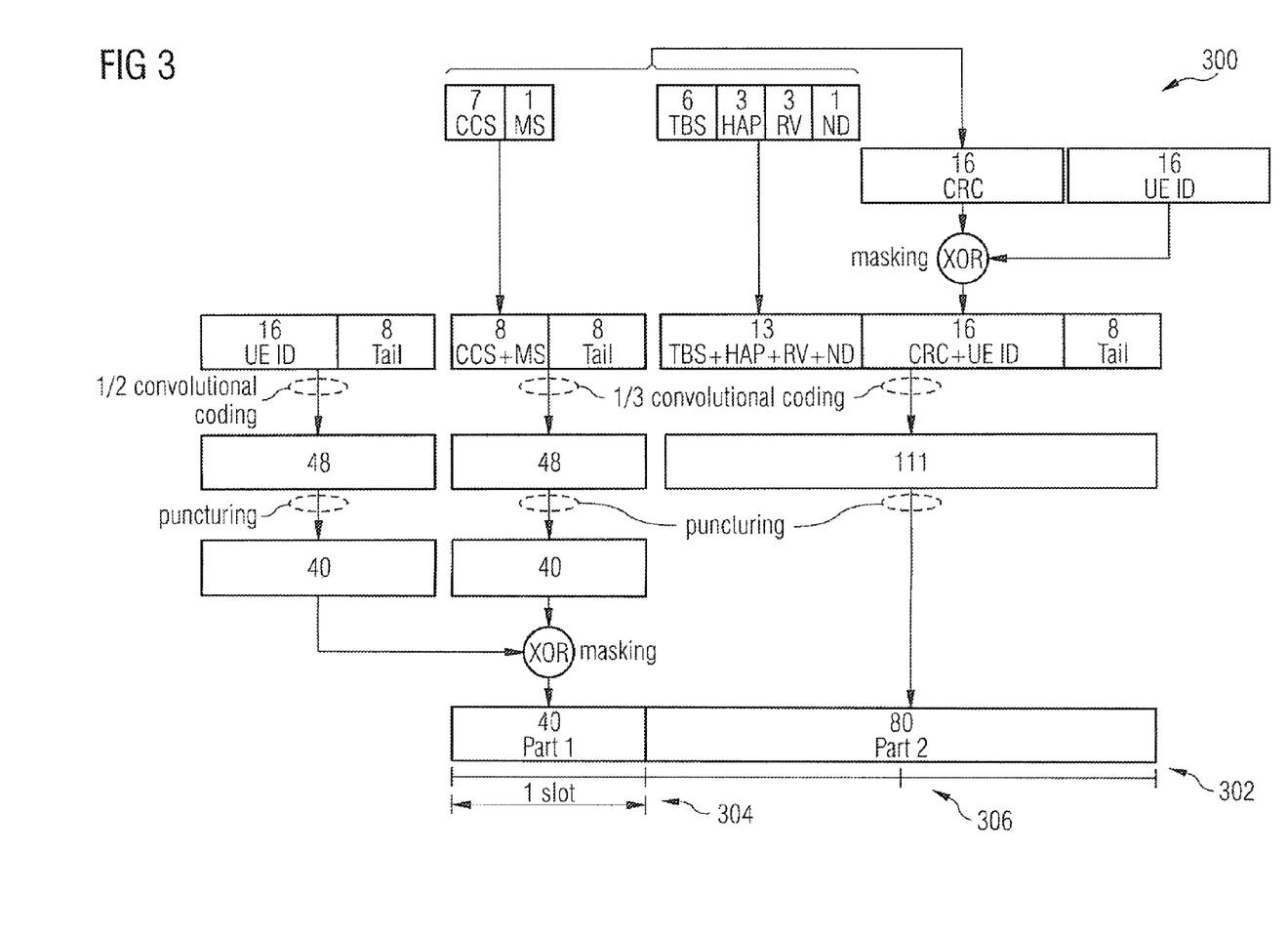
FIG. 3 schematically depicts an example of a type-1 HS-SCCH coding chain according to the disclosure.

FIG. 3 is a schematic representation of a type-1 HS-SCCH coding chain 300 illustrating a number of bits at each encoding stage. On the input side a CCS (Channelization Code Set) may comprise 7 bits, an MS (Modulation Scheme) indication may comprise 1 bit, a TBS (Transport Block Size) indication may comprise 6 bits, a HAP (Hybrid ARQ Process) indication may comprise 3 bits, an RV (Redundancy and constellation Version) indication may comprise 3 bits, an ND (New Data) indicator may comprise 1 bit, a CRC field may comprise 16 bits, and for the indication of UE ID (identity), 16 bits may be reserved. After convolutional coding and puncturing, and a masking step for the part 1 transmission, the indicated data sequence may be transmitted via SCCH 302. A part-1 transmission of SCCH 302 in slot 1 (304) may comprise 40 bits, while a part-2 transmission in slots 2 and 3 (306) may comprise 80 bits.

Figure 4:
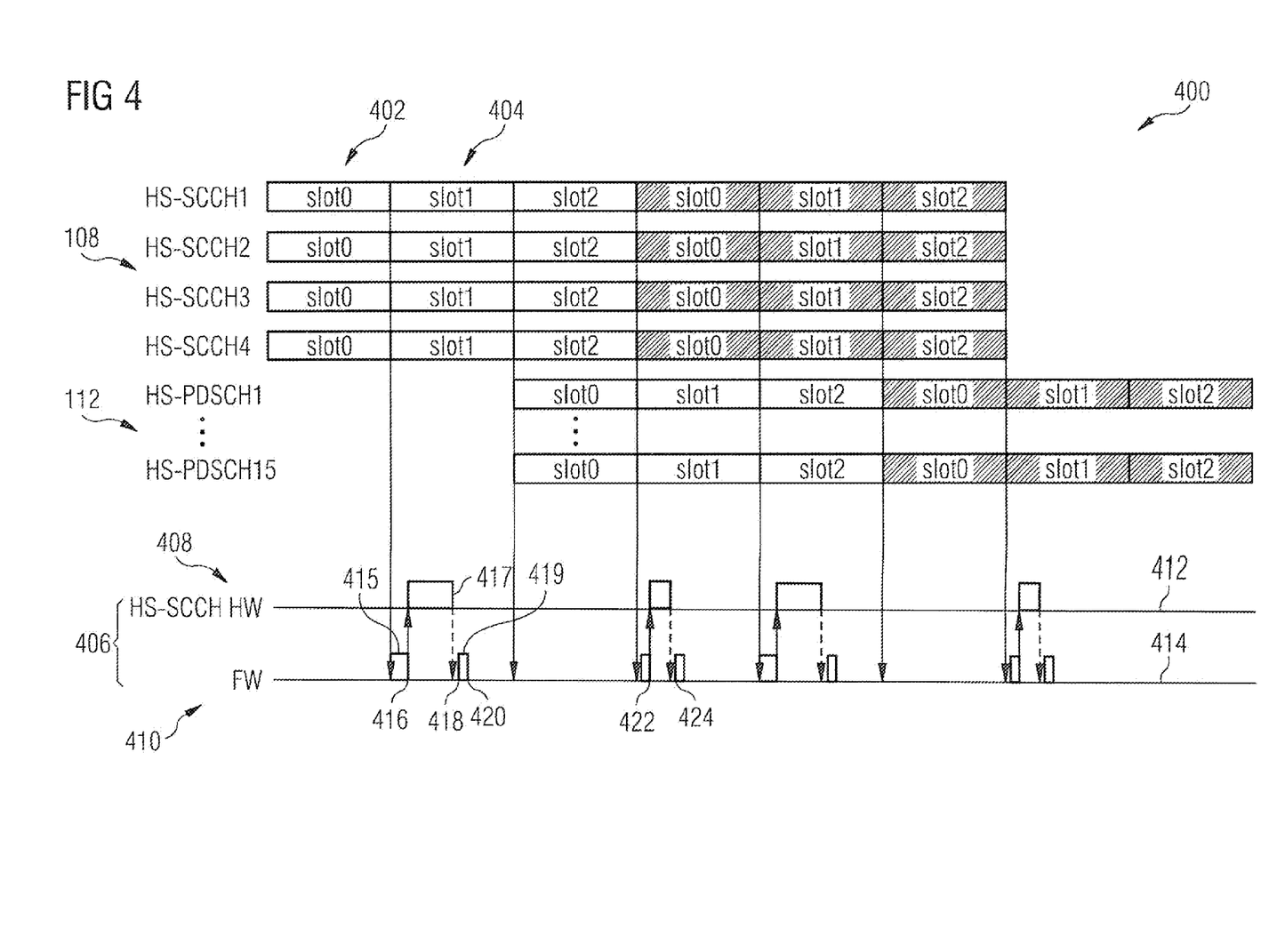
FIG. 4 is an example of a timing diagram on an air interface of a mobile communications system together with a possible HW-FW split according to the disclosure.

FIG. 4 illustrates a timing scheme which may be applied to the HS-SCCH 108 and associated PDSCH 112 of FIG. 1. The four parallel control channels SCCH1 to SCCH4 may be transmitted two time slots ahead the corresponding data channels PDSCH1 to PDSCH15, which may be allow the receiving part of the UE 104 to be configured for the data reception. By way of example, in a control channel slot0 of a current subframe 402, part-1 control information may be transmitted, such as that illustrated with the first part 204 in FIG. 2. In slot1 and slot2 of a current subframe 404, part-2 information may be transmitted, such as that illustrated with the second part 206 in FIG. 2. The part-2 information may be less time critical than the part-1 information.

A receiving part 406 of UE 104 is schematically represented in FIG. 4 by a hardware (HW) component 408 and a firmware (FW) component 410. Operation of the components 408 and 410 at given times is indicated along lines 412 and 414, respectively. At 416 following the end of current time slot0 402, the FW component 410, upon complete reception and demodulation of the slot0 402 transmission in all control channels SCCH1 to SCCH4 indicated with an operational block 415 in FIG. 4, may configure and start the part-1 HW component 408 to perform part-1 decoding, by means of the known dedicated UE-ID, for each of the four received part-1 channels. The part-1 decoding (operational block 417) may comprise an inverse bit-processing, which in turn may comprise, with reference to part 204 in FIG. 2, an UE-specific de-masking, de-rate matching, channel decoding, etc. for all control channels 108 to be monitored.

At 418, the HW component 408 may deliver the decoded payload, and may further deliver detection metrics for the four decoded part-1 control channels. The computed metrics may support the detection of the proper HS-SCCH. Until 420, the FW component 410 may have executed a detection algorithm (operational block 419) to detect the most probable of the received up to four control channels 108. According to various embodiments, the detection of the proper control channel in block 419 may be performed in firmware for a maximum of flexibility.

The detection algorithm may be performed on the basis of, among others, the metrics delivered by the decoding HW 408 for each of the control channels SCCH1 to SCCH4. For example, the index of the control channel with a maximum metric (or a minimum metric) may be determined. As a preparatory step, each of the metrics may be compared against a threshold, and the maximum (or minimum) metric may be chosen only from those metrics, if any, which are at least above (or below) the threshold. The threshold may be a predefined or fixed threshold; for example, a fixed threshold may be optimally selected to prevent a false alarm. Additionally or alternatively, the threshold may be a configurable or dynamic threshold; for example, the threshold may be adapted to an average received signal amplitude, and/or may be adapted to minimize simultaneously $P_{md}$ and $P_{fa}$.

At 422 after complete reception of slot1 and slot2 of the selected control channel, the FW component 410 may configure and start a part-2 HW component, which may be assumed to be the HW component 408 purely for simplicity in FIG. 4, to decode the received part-2 data, which have been illustrated, for example, by part 206 in FIG. 2. At 424 the HW component 408 may deliver the decoded part-2 payload and a CRC result to the FW component 410. In case of a false alarm, which may be detectable based on the CRC result, the decoded payload may be discarded.

A reliable part-1 detection before and at 416, 418, and/or 420 may be essential for an optimum system performance. For example, missed detections due to non-selection of any control channel or wrong selection of the proper control channel may reduce the throughput. False detections may trigger unnecessary reception processing wherein the received data may be aborted after CRC check in part-2. The reception processing may waste terminal resources and increases power consumption.

According to various embodiments of detection processes, improvements focused on minimizing $P_{md}$ can be desirable due to the direct impact on throughput. Other embodiments may focus on a joint optimization of $P_{md}$ and $P_{fa}$. Various approaches which may be used as a basis for both kinds of embodiments will be discussed below. Generally, these approaches can be implemented by means of the HW 408 and FW 410 components illustrated in FIG. 4, for example, by adapting existing HW/FW components, focused on the operational blocks 415, 417 and/or 419.

Figure 5:
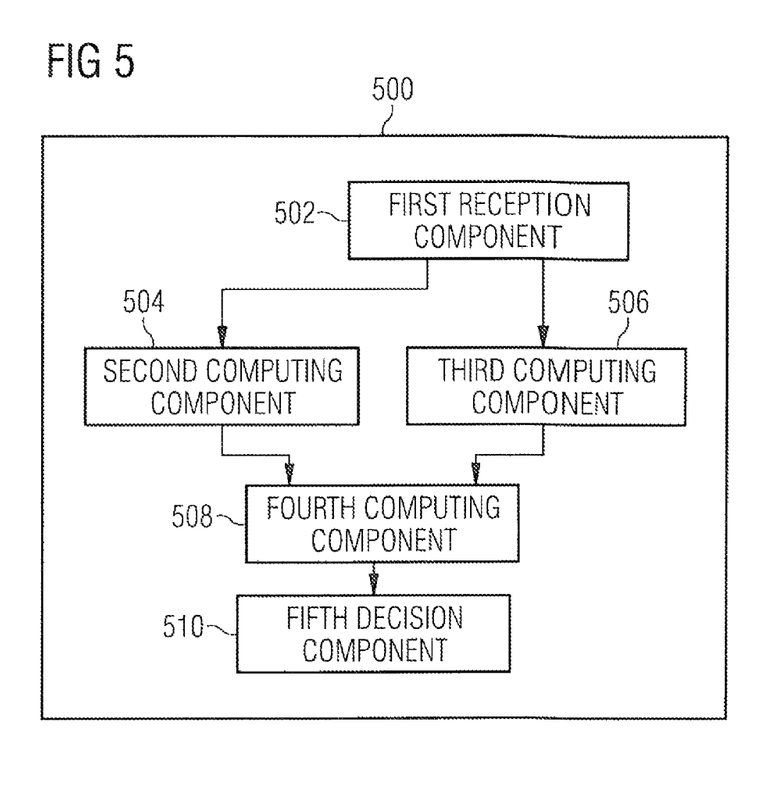
FIG. 5 is an example of a flow diagram illustrating a first embodiment of a control channel detection procedure according to the disclosure.

FIG. 5 schematically illustrates functional building blocks or components of a device 500 for detecting a control channel such as, for example, an SCCH in a HSDPA system. The device 500 may be an implementation of a receiving part of the UE 104 of FIG. 1, or of the HW 408/FW 410 components in FIG. 4. The device 500 may comprise a first reception component 502, which may be configured to receive data transmitted via a control channel. A second computing component 504 may be configured to compute a path metric based on the received data. A third computing component 506 may be configured to compute a correction term based on the received data. A fourth computing component 508 may be configured to compute a decision metric. A fifth decision component 510 may be configured to decide on a detection of the control channel.

Figure 6:
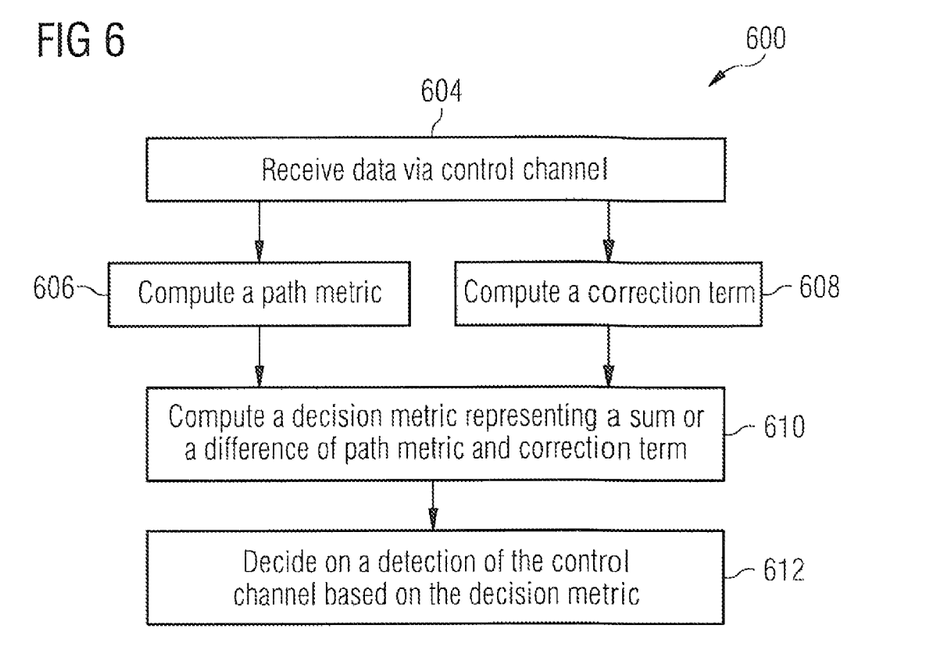
FIG. 6 is a functional block diagram illustrating an example of a device for implementing the procedure of FIG. 5 according to the disclosure.

An operational mode 600 of device 500 will be discussed with reference to the flow diagram depicted in FIG. 6. In 604 the reception component 502 may operate to receive data transmitted via a control channel. The control channel may be one or more of the channels 108 illustrated in FIGS. 1 and 4. In step 606 the computing component 504 may operate to compute a path metric based on the received data. Concerning the path metric, one can compute the Viterbi path metric or one can compute in a more general sense an accumulated path metric in one embodiment. One special accumulated path metric may be the maximum likelihood (ML) path metric. Generally speaking, one or more of a maximum likelihood path metric, an accumulated path metric, and a Viterbi path metric may be computed. The computation may also comprise multiplying a path metric with a weighting factor. The weighting factor may be indicative of a signal strength of the received data in one embodiment.

In 608, which may be performed in parallel with step 606, the computation component 506 may operate to compute a correction term based on the received data. The correction term may be indicative of a signal strength of the received data. Step 608 may comprise performing a summing operation on vector elements of a received softbit data vector. For example, the summing operation may comprise applying a function on each of the vector elements, such as performing a multiplication with a weighting factor, applying a logarithm, a hyperbolic cosine, absolute value function, and a squaring function, and/or any approximations thereof.

In 610 the computing component 508 may operate to compute a decision metric based on an output of the components 504 and 506. For example, the decision metric may represent a sum or a difference of the path metric computed by the component 504 and the correction term computed by the component 506. At 612 the component 510 may decide, based on the decision metric, on a detection of the control channel. 612 may comprise, for example, comparing the computed decision matrix to a threshold, which may be a fixed or dynamic threshold. A detection decision may be found based on a result of the comparison. According to various embodiments, the decision process may comprise comparing a plurality of decision metrics derived for a plurality of control channels.

The components of device 500 may be implemented in hardware and/or software/firmware. Which functions are advantageously to be implemented in HW or FW may depend on the specific circumstances of a particular application. Various considerations, which may be relevant in this respect, are spread throughout the discussions herein.

Figure 7:
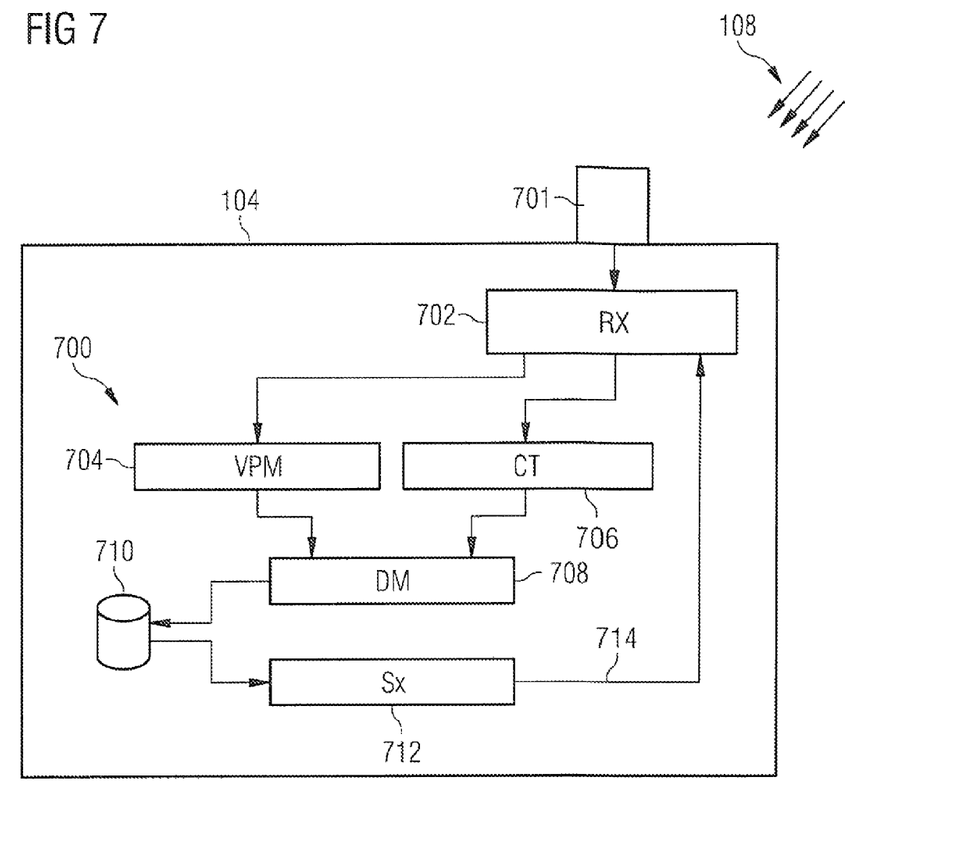
FIG. 7 is an example of a flow diagram illustrating a second embodiment of a control channel detection procedure according to the disclosure.

FIG. 7 is a functional block diagram illustrating components of an embodiment 700 of a device for selecting a control channel from a plurality of control channels. The device 700 may be an implementation of a receiving part of UE 104 of FIG. 1, of the HW 408/FW 410 components in FIG. 4, and/or of device 500 of FIG. 5. For exemplary reference, control channels 108 of FIG. 1 are indicated in FIG. 7.

A first reception component (Rx) 702 of device 700 may be configured to receive data transmitted via the plurality of control channels. Second and third computing components (VPM (virtual parallel machine), CT (computer terminal)) 704 and 706 may be configured to compute a path metric and a correction term, respectively, for each of the plurality of control channels. A fourth computing component (DM) 708 may be configured to compute a decision metric for each of the plurality of control channels. A fifth selection component (Sx) may be configured to select one of the plurality of the control channels.

An operational mode 800 of device 700 is now discussed with reference to the flow diagram of FIG. 8. Control may be handed over at starting point 802 from a higher level to the processing depicted in FIG. 8, which regards selecting a control channel from a plurality of control channels. At 804, the reception component 702 may receive data, which may be transmitted via the plurality of control channels and may be received via antennas 701 of UE 104. With exemplary reference to the lines 412 and 414 in FIG. 4, part-1 data may be received in slot0 402 from the channels SCCH1 to SCCH4.

The reception component 702 may initiate 806 by triggering the computing components 704 and 706 for computing a path metric, for example a Viterbi path metric, and a correction term, respectively, for each of the plurality of control channels in 806. The trigger may comprise providing at least portions of the received data to the components 704 and 706. Either or both of the reception process 804 and the computing processes 806 may include de-modulating the received data.

The components 704 and 706 deliver their computation results to the further computing component 708, which in 808 operates to compute a decision metric for each of the plurality of monitored/received control channels 108. The plurality of computed decision metrics may be buffered for further processing in a storage area 710 associated with receiving part 700 in UE 104. Computing a decision metric may comprise, for example, applying a channel-specific weighting factor to at least one of the channel-specific path metric and the correction term. By way of example, such weighting factors may comprise a channel-specific signal amplitude and/or a channel-specific signal variance. Additionally or alternatively, similar or other weighting factors can be applied later in the process.

In 810 the selection component 712 may select one of the plurality of received control channels 108. The selection may be based on the plurality of decision metrics buffered in storage area 710. The selection process may comprise applying a channel-specific weighting factor to a decision metric, wherein the weighting factor may, for example, represent a signal-to-noise ratio, a signal power, etc., related to the corresponding control channel. The decision metrics may be made the subject of a maximum or a minimum search. According to one embodiment, each of the computed decision metrics may be compared to a threshold, and only those metrics may be considered for the maximum or minimum search, which are above or below, respectively, the threshold.

After selecting a control channel, the method 800 may end by returning control back to a higher level at end point 812. The return procedure may comprise providing at 714 an indication of the selected control channel to the higher level control for focusing reception of part-2 data to the selected of the control channels.

According to various embodiments, a Viterbi decoder metric may be available after a decoding of received data and may be re-used for computing the path metric in 806. In this case, an implementation of, for example, the process 800 may require a minimum of additional software/firmware code and/or hardware circuitry. In other embodiments, in which no metric is used for decoding or is no longer available after decoding, an accumulated Viterbi metric may have to be (re-)constructed, which may require an additional hardware circuitry and/or firmware coding for re-encoding, soft-bit weighting and accumulation.

Generally, a Viterbi algorithm can provide for a final accumulated metric for each state at the end of a forward recursion. State metrics may reflect the Euclidian distance between a received signal and the most likely code words in a trellis diagram. Viterbi metrics can increase with the amplitude of a received control channel, for example, the Signal-to-Noise Ratio SNR, for example in fading conditions, if the control channels are power controlled by the nodeB independently of each other, etc.

Various embodiments of the present disclosure may implement a maximum-likelihood (ML) detection process for detecting, for example, a part-1 control channel in a HSDPA scenario. The ML detection approach may be based on an approximate signal model. An example for a signal model is described below. Based on such signal model, an optimum decision metric may comprise, for example, a properly weighted accumulated maximum-likelihood Viterbi-path metric and a correction term, wherein the correction term may have to be added to or substracted from the path metric. Such decision metric has to be computed for each control channel hypothesis. A final maximum search may then be performed for detecting the most probable control channel.

The approach of calculating a metric for each received control channel and performing a maximum search among all metrics may lead to an optimized (i.e., minimized) missed detection rate $P_{md}$, while the probability for false alarm $P_{fa}$ can be disregarded. This solution can be acceptable due to the higher significance of $P_{md}$ for user throughput. In order to jointly optimize both probabilities $P_{md}$ and $P_{fa}$, according to one embodiment a threshold can be applied in the detection algorithm, wherein the threshold may be applied prior to the maximum (or minimum) search.

An example for a signal model of part-1 HS-SCCH reception after equalization, despreading and QPSK demodulation may approximately be given by $$y_l^{(i)} = A_i * x_l^{(i)} * u_l^{(i)} + n_l^{(i)}, l=1,2,\ldots,40, \quad (1)$$

where $\vec{y}^{(i)} = (y_1^{(i)}, \ldots, y_{40}^{(i)})$ denotes the length-40 received softbit vector of the i-th HS-SCCH, $A_i$ the signal amplitude in the current part-1 slot, $\vec{x}^{(i)} = (x_1^{(i)}, \ldots, x_{40}^{(i)})$ denotes the encoded and rate-matched binary code word of the i-th HS-SCCH ($x = +-1$), $\vec{u}^{(i)} = (u_1^{(i)}, \ldots, u_{40}^{(i)})$ denotes the encoded and rate-matched H-RNTI (UE-ID) vector of the i-th HS-SCCH ($u = +-1$), and $\vec{n}^{(i)} = (n_1^{(i)}, \ldots, n_{40}^{(i)})$ denotes a length-40 vector of white Gaussian noise samples of variance $\sigma_i^2$.

The k-th HS-SCCH may be regarded as the HS-SCCH which is intended for the UE, while the remaining ($N_{scch}-1$) HS-SCCHs (i=1, ..., $N_{scch}$; i<>k) may be the HS-SCCHs not intended for the UE. The known UE-ID of the UE in equation (1) may be represented as $\vec{u} = (u_1, \ldots, u_{40})$ for which a superscript index may be omitted. The signal model for the HS-SCCH intended for the UE may then be written as $$y_l^{(k)} = A_k * x_l^{(k)} * u_l + n_l^{(k)}. \quad (2)$$

Assuming that the data vector $\vec{x}^{(i)}$ scrambled with the unknown UE-ID $\vec{u}^{(i)}$ renders the sequences $\vec{b}^{(i)} \stackrel{def}{=} \vec{x}^{(i)} * \vec{u}^{(i)} = (x_1^{(i)} * u_1^{(i)}, \ldots, x_{40}^{(i)} * u_{40}^{(i)})$ into independent and identically distributed (IID) binary random sequences for i=1, ..., $N_{scch}$; i<>k, equation (2) can be rewritten as $$y_l^{(k)} = A_k * b_l^{(k)} + n_l^{(k)}. \quad (3)$$

By averaging out the random binary sequences from the conditional probability distributions, the following ML (Maximum Likelihood)-detection rule may be arrived at:

$$\text{argmax}_{i=1,\ldots,N_{scch}} \max_{\vec{x} \in C} \underbrace{\frac{A_i}{\sigma_i^2} \sum_{l=1}^{40} y_1^{(i)} x_1^{(i)} u_1}_{\text{re-encoded path-metric}} - \underbrace{\sum_{l=1}^{40} \text{logcosh}\left(\frac{A_i}{\sigma_i^2} y_1^{(i)}\right)}_{\text{correction term}}. \quad (4)$$

Defining $$\text{ML\_A}_i = \max_{\vec{x} \in C} \sum_{l=1}^{40} y_1^{(i)} x_1^{(i)} u_1 \quad (5)$$

and $$\text{ML\_B}_i = \sum_{l=1}^{40} \text{logcosh}\left(\frac{A_i}{\sigma_i^2} y_1^{(i)}\right), \quad (6)$$

the decision rule can be rewritten as $$\text{argmax}_{i=1,\ldots,N_{scch}} \frac{A_i}{\sigma_i^2} \text{ML\_A}_i - \text{ML\_B}_i. \quad (7)$$

Figure 8:
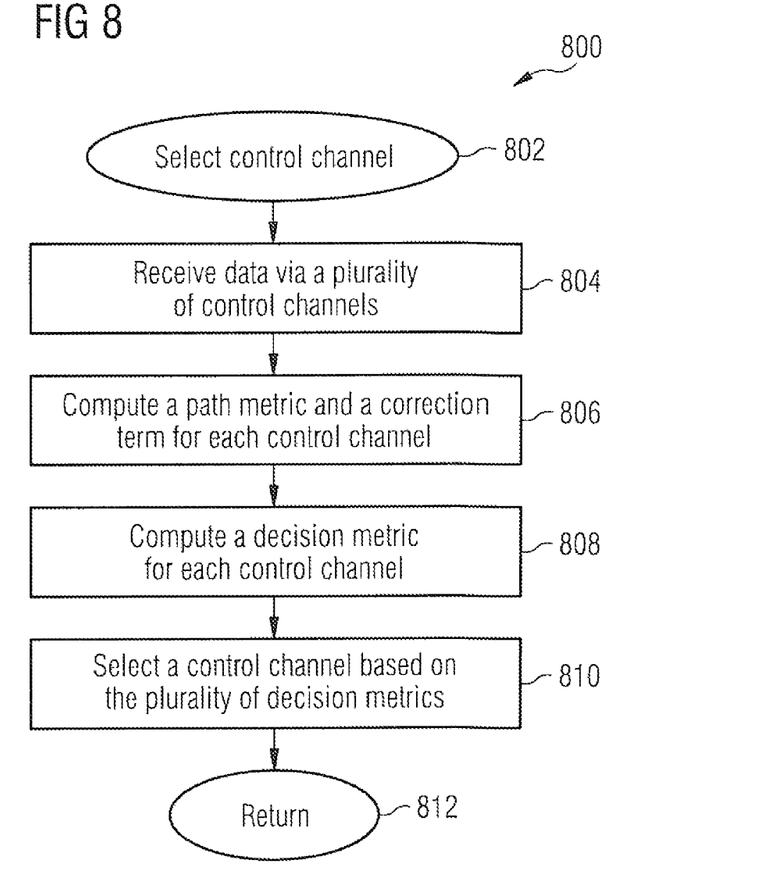
FIG. 8 is an example of a functional block diagram illustrating a device for implementing the procedure of FIG. 7 according to the disclosure.
Figure 9:
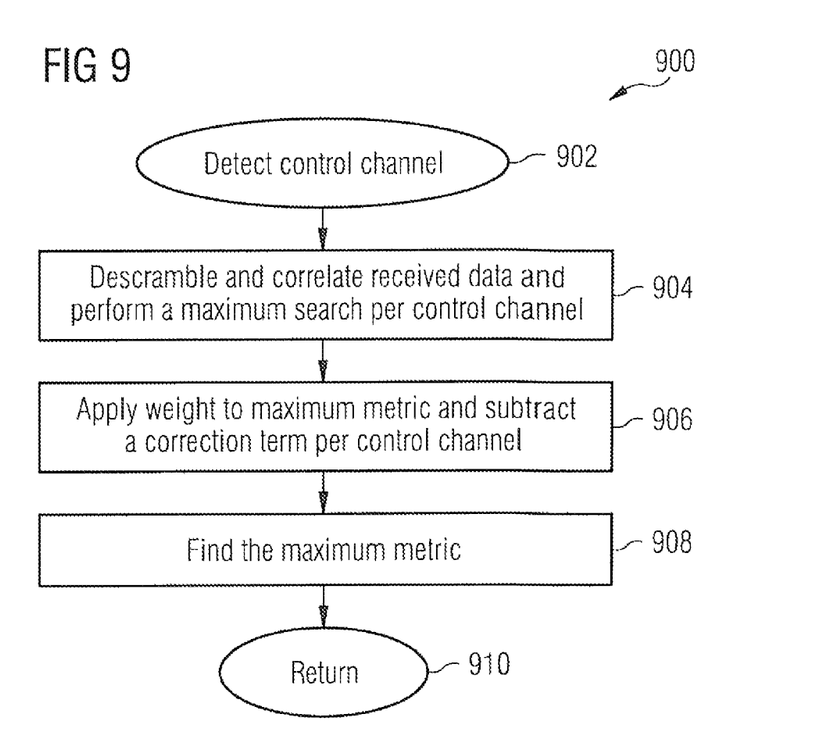
FIG. 9 is an example of a flow diagram illustrating a third embodiment of a control channel detection procedure according to the disclosure.

FIG. 9 is a flow diagram illustrating an embodiment 900 of a detection procedure for detecting a control channel. The procedure 900 may be an implementation of part or all of the process 600 of FIG. 6 and/or the process 800 of FIG. 8. The detection procedure may implement aspects related to equation (4) above.

At a starting point 902, control may be handed over from a higher level, for example from a control procedure related to 606 to 612 in FIG. 6 or 806 to 810 in FIG. 8. At 904, all received sequences $\vec{y}^{(i)} = (y_1^{(i)}, \ldots, y_{40}^{(i)})$ may be descrambled with the known UE-ID-vector $\vec{u} = (u_1, \ldots, u_{40})$ and correlated with all possible code-sequences $\vec{x}^{(i)} = (x_1^{(i)}, \ldots, x_{40}^{(i)})$. The maximum among all code sequences $\vec{x}^{(i)} \in C$ may be determined. The set C may correspond to the set of all possible binary encoded and rate-matched HS-SCCH length-40 codewords whose cardinality is $2^8=256$ for type 1 and $2^{12}=4096$ for type 3, respectively.

According to various embodiments, the first term in equation (4), i.e., the term ML_A in equation (5) may be computed by a Viterbi algorithm employed, for example, for de-coding. According to particular implementations, the full path-metric may be available in the zero-state at the end of the trellis. In other implementations, the path-metric may need to be determined fully or in part by re-encoding, rate matching, and softbit-weighting of the hard-decoded sequence of the Viterbi algorithm.

At 906, the resulting $N_{scch}$ maximum metrics may be each weighted with a factor $$\frac{A_i}{\sigma_i^2}$$

and a respective correction term may be subtracted to arrive at a decision metric, as illustrated in equation (4) or equations (6) and (7). According to particular implementations, the weighting factor $$\frac{A_i}{\sigma_i^2}$$

may already be included in the softbit vectors $\vec{y}^{(i)}$ before running a Viterbi algorithm. The inputs to the weighting factor itself may be determined by estimating amplitude and variance of the signal using methods known to the skilled artisan. According to various embodiments, the second term in equation (4), i.e., the term ML_B in equation (6), may be evaluated in parallel to a Viterbi algorithm, for example, by means of a lookup table.

At 908, the detected HS-SCCH and the corresponding payload may be determined by finding the index attaining the maximum over the $N_{scch}$ (decision) metrics from 904. Control may be returned to higher level at point 910.

According to various embodiments, a different, e.g., simplified, correction term may be implemented. Approximations in this respect may be based on that, e.g., for a high SNR a term log(cos h(x)) may be approximately equal to x-log(2) while for low SNR the term behaves as $0.5x^2$.

A robust detection rule may be defined by $$\text{arg max}_{i=1,\ldots,N_{scch}} (\text{ML\_A}_i - \text{ML\_C}_i) * Q_i, \quad (8)$$

where $$\text{ML\_C}_i = \Sigma_{l=1}^{40} |y_l^{(i)}| \quad (9)$$

may be seen as an approximated correction term and $Q_i$ is, for example, a function of the SNR or the signal power $S_i$ of the i-th HS-SCCH.

Various exemplary definitions for the channel-specific weighting factor $Q_i$ may comprise:

$$Q_i = SNR_i^{-1}$$

$$Q_i = S_i^{-1}$$

$$Q_i = \sqrt{SNR_i}^{-1}$$

$$Q_i = \sqrt{S_i}^{-1}$$

The various detection procedure embodiments above aim at optimizing the probability of missed detection $P_{md}$. In order for a joint optimization of both $P_{md}$ and $P_{fa}$, a detection procedure may be modified by introducing a threshold, for example, prior to 908 in FIG. 9, and by selecting the maximum of only those HS-SCCHs exceeding the threshold (or falling below the threshold).

Figure 10:
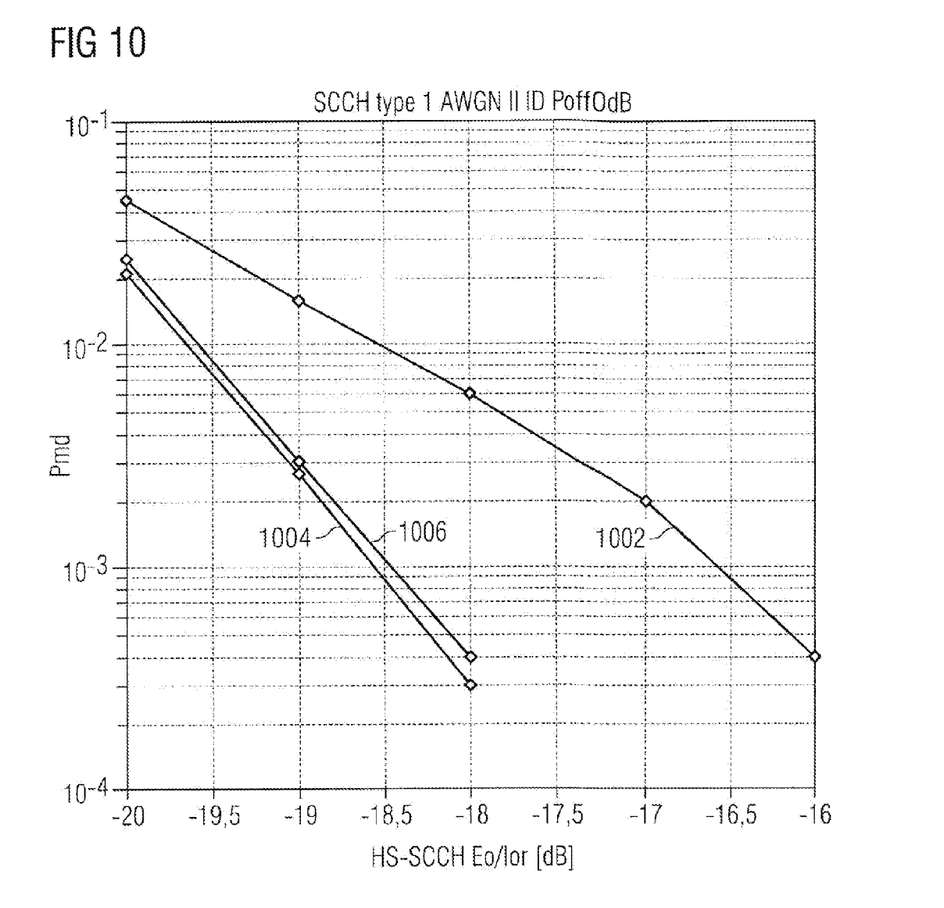
FIG. 10 is an example of a diagram illustrating rates of missed detection for various control channel detection procedures in an AWGN scenario according to the disclosure.

FIG. 10 illustrates the probability of missed detection $P_{md}$ for detecting a HS-SCCH in a HSDPA framework for various detection processes based on an AWGN (Additive White Gaussian Noise) scenario. The detection rates are measured for a scenario following FIG. 1, wherein four part-1 control channels are transmitted in slot0 with equal power. Graph 1002 shows the missed detection rate for a typical conventional detection process, which may be based, for example, on a bit error rate. Graph 1004 illustrates a missed detection rate for an implementation of process 900 according to equation (4) as described above. Graph 1006 illustrates a missed detection rate for an implementation of an approximate detection rule as discussed above with reference to equation (8) with $Q_i = \sqrt{S_i}^{-1}$. It is illustrated that, for example for a signal strength of around −18 dB, the missed detection rate for the implementations leading to graphs 1004, 1006 are lowered by more than a factor of 10 compared to the conventional detection procedure 1002.

FIGS. 5 and 7 show example implementations from a functional point of view. It will be appreciated that the functionalities illustrated by the various function blocks may be implemented on the basis of dedicated hardware circuitry such as dedicated ICs (Integrated Circuits), chips, etc., and/or on the basis of firmware/software functioning operated on a general purpose computing/processing facility such as, for example, programmable ICs or chips, DSPs (Digital Signal Processors), ASICs (Application Specific Integrated Circuits), etc.

Various approaches of splitting the various functionalities into HW circuitry on the one hand and FW (or software) programming on the other hand may be contemplated according to the details of particular applications. With exemplary reference to the embodiments described in FIGS. 7 and 8 it is noted that the computations of 806 and/or 808 may be performed, for example, in blocks 417 and/or 419 illustrated in FIGS. 4. 808 and 810 may, for example, be performed in block 419.

Consequently, and according to one exemplary, non-limiting embodiment, the reception component 702 may be implemented as part of the firmware 410, while the component 704 for computing the path metrics may be implemented as part of the hardware 408. The component 706 for computing the correction term may also be implemented as part of the hardware 408, and may therefore be considered as an augmentation or an add-on to the implementation of component 704. According to other embodiments, the component 706 may be implemented in firmware. The component 708 for computing the decision metrics and the selection 712 may be implemented in firmware for reasons of cost-efficiency and/or in order to achieve an optimum flexibility with regard to, for example, application of a dynamic threshold, application of various different approximate detection methods as described herein, etc.

A firmware, software, or any other computer program product to be employed in one or more of the embodiments discussed herein may comprise program code portions for performing at least a portion of one or more of the method or process aspects described, when the computer program product is executed on a computing device such as, for example, a receiving part of a terminal device, UE, user terminal, mobile phone, etc.

The computer program product may be stored on a computer readable recording medium such as a permanent or semi-permanent or re-writeable memory within or associated with a computing device. Embodiments of memories may comprise, for example, a RAM (Random Access Memory), ROM (Read Only Memory), EPROM (Erasable Programmable ROM), a removable CD-ROM, DVD, an USB-stick, etc., as long as a software/firmware coding of a method or method aspect as described herein could be stored with such media. Additionally or alternatively, the computer program product may be provided for download to a computing device, for example via a data network such as the Internet and/or a communication line such as a telephone line or a wireless link.

While specific embodiments have been illustrated and described herein, it will be appreciated by those of normal skill in the art that many modifications may be made, adaptations be performed and variants be implemented in view of the specific embodiments shown and described. Accordingly, it is intended that any such modifications, adaptations and variations of the specific embodiments discussed herein are covered and the invention be limited only by the scope of the appended claims.

For example, while a particular aspect or feature of an embodiment of the present disclosure may have been described with respect to only one of several implementations, such aspect or feature may be combined with one or more other aspects or features of the other implementations as may be desired and advantageous for any given or particular application.

With regard to the various functions performed by the above-described components or structures (assemblies, devices, circuits, systems, etc.), the terms (including a reference to "means") used to describe such components are intended to correspond, unless otherwise indicated, to any component or structure which performs the specified function (e.g., that is functionally equivalent), even though not structurally equivalent to the disclosed structure which performs the function in the herein illustrated exemplary implementations.

As used herein, to the extent that terms such as "include", "have", "with", or variants thereof are used in either the detailed description or the claims, it is to be understood that such terms are intended to be inclusive in a manner similar to the term "comprise". The term "exemplary" or variants thereof are meant to merely denote one or an example, rather than the best or optimum example according to any given criterion.

The invention claimed is:

1. A method of detecting a control channel, comprising:
receiving data transmitted via a control channel;
computing a path metric based on the received data;
computing a correction term based on the received data;
computing a decision metric representing a sum or a difference of the path metric and the correction term; and
deciding, based on the decision metric, on a detection of the control channel,
wherein deciding on a detection of the control channel comprises comparing the decision metric to a threshold and deciding on a detection based on a result of the comparison.

2. The method of claim 1, wherein computing the path metric comprises computing a maximum likelihood path metric based on the received data.

3. The method of claim 1, wherein computing the path metric comprises computing an accumulated path metric based on the received data.

4. The method of claim 1, wherein computing the path metric comprises computing a Viterbi path metric based on the received data.

5. The method of claim 1, wherein computing the path metric further comprises multiplying the path metric with a weighting factor indicative of a signal strength of the received data.

6. The method of claim 1, wherein the correction term is indicative of a signal strength of the received data.

7. The method of claim 1, wherein computing the correction term comprises performing a summing operation on vector elements of a received soft-bit data vector.

8. The method of claim 7, wherein the summing operation comprises applying a first function on each vector element.

9. The method of claim 8, wherein the first function comprises one or more of a multiplication with a weighting factor, a logarithm, a hyperbolic cosine, an absolute value function, and a squaring function, or approximations thereof.

10. The method of claim 1, wherein the path metric and the correction term are computed in parallel.

11. A method of selecting a control channel from a plurality of control channels, comprising:

receiving data transmitted via the plurality of control channels;

computing, based on the received data, a path metric and a correction term for each of the plurality of control channels;

computing, for each of the plurality of control channels, a decision metric representing a sum or a difference of the path metric and the correction term; and selecting, based on the plurality of computed decision metrics, a control channel from the plurality of control channels, wherein selecting a control channel comprises:
comparing each of the plurality of computed decision metrics to a threshold, and
selecting the control channel based on those decision metrics which passed the comparison.

12. The method of claim 11, wherein computing the decision metric comprises applying a channel-specific weighting factor to at least one of the path metric and the correction term.

13. The method of claim 12, wherein the weighting factor represents a channel-specific signal strength.

14. The method of claim 13, wherein the weighting factor represents a channel-specific signal amplitude and/or a channel-specific signal variance of the received data.

15. The method of claim 13, wherein the weighting factor comprises a function representing a signal-to-noise ratio and/or a signal power of a corresponding control channel.

16. The method of claim 15, wherein the weighting factor comprises an inverse of the function or of a square root of the function or another function $x^p$ where x is the function and p is any real number.

17. The method of claim 13, wherein selecting a control channel comprises selecting a High Speed Shared Control Channel (HS-SCCH) in a High Speed Downlink Packet Access (HSDPA) system.

18. A computer program product having computer executable instructions stored in a non-transitory storage medium, and upon executing the instructions in conjunction with a processor, operable to perform a method, comprising:
receiving data transmitted via the plurality of control channels at a receiver circuit;
computing, based on the received data, a path metric and a correction term for each of the plurality of control channels using a processor circuit;
computing, for each of the plurality of control channels, a decision metric representing a sum or a difference of the path metric and the correction term using the processor circuit; and selecting, based on the plurality of computed decision metrics, a control channel from the plurality of control channels, wherein selecting a control channel comprises:
comparing each of the plurality of computed decision metrics to a threshold, and
selecting the control channel based on those decision metrics which passed the comparison.

19. A device for detecting a control channel, comprising:
a first component configured to receive data transmitted via a control channel;
a second component configured to compute a path metric based on the received data;
a third component configured to compute a correction term based on the received data;
a fourth component configured to compute a decision metric representing a sum or a difference of the path metric and the correction term; and
a fifth component configured to decide, based on the decision metric, on a detection of the control channel,
wherein deciding on a detection of the control channel comprises comparing the decision metric to a threshold and deciding on a detection based on a result of the comparison.

20. A device for selecting a control channel from a plurality of control channels, comprising:
a first component configured to receive data transmitted via the plurality of control channels;
a second component configured to compute, based on the received data, a path metric and a correction term for each of the plurality of control channels;
a third component configured to compute a decision metric representing a sum or a difference of the path metric and the correction term for each of the plurality of control channels; and
a fourth component configured to select, based on the plurality of decision metrics, a control channel from the plurality of control channels, wherein selecting a control channel comprises:
comparing each of the plurality of computed decision metrics to a threshold, and
selecting the control channel based on those decision metrics which passed the comparison.

21. The device of claim 20, wherein one or more of the components are implemented in firmware and/or hardware.

* * * * *